United States Patent
Naushad et al.

(10) Patent No.: US 9,987,617 B1
(45) Date of Patent: Jun. 5, 2018

(54) CARBOXYLIC FUNCTIONALIZED MAGNETIC NANOCOMPOSITE

(71) Applicant: KING SAUD UNIVERSITY, Riyadh (SA)

(72) Inventors: Mu Naushad, Riyadh (SA); Ayoub Abdullah Alqadami, Riyadh (SA); Tansir Ahamad, Riyadh (SA); Zeid Abdullah Alothman, Riyadh (SA); Saad M. Alshehri, Riyadh (SA)

(73) Assignee: KING SAUD UNIVERSITY, Riyadh (SA)

(*) Notice: Subject to any disclaimer, the term of this patent is extended or adjusted under 35 U.S.C. 154(b) by 0 days. days.

(21) Appl. No.: 15/722,898

(22) Filed: Oct. 2, 2017

(51) Int. Cl.
| | |
|---|---|
| B01D 39/00 | (2006.01) |
| C02F 1/28 | (2006.01) |
| B01J 20/22 | (2006.01) |
| B01D 15/00 | (2006.01) |
| B01J 20/28 | (2006.01) |
| C07F 15/02 | (2006.01) |
| B01J 20/06 | (2006.01) |
| C02F 1/66 | (2006.01) |
| B01J 20/32 | (2006.01) |
| B01D 24/00 | (2006.01) |
| B01J 20/00 | (2006.01) |
| C02F 101/30 | (2006.01) |

(52) U.S. Cl.
CPC ......... *B01J 20/28009* (2013.01); *B01J 20/06* (2013.01); *B01J 20/22* (2013.01); *B01J 20/28016* (2013.01); *B01J 20/3293* (2013.01); *C02F 1/285* (2013.01); *C02F 1/288* (2013.01); *C02F 1/66* (2013.01); *C07F 15/025* (2013.01); *C02F 2101/308* (2013.01); *C02F 2303/16* (2013.01)

(58) Field of Classification Search
None
See application file for complete search history.

(56) References Cited

U.S. PATENT DOCUMENTS

| | | |
|---|---|---|
| 7,547,473 B2 | 6/2009 | Chen et al. |
| 8,221,622 B2 | 7/2012 | Fukaya et al. |
| 9,334,176 B1 | 5/2016 | Alshehri et al. |

(Continued)

OTHER PUBLICATIONS

Kralj et al. "Controlled surface functionalization of silica-coated magnetic nanoparticles with terminal amino and carboxyl groups", J. Nanopart Res, 2011, 13, 2829-2841.*

(Continued)

*Primary Examiner* — Clare M Perrin
(74) *Attorney, Agent, or Firm* — Richard C. Litman

(57) ABSTRACT

Carboxylic functionalized magnetic nanocomposites can include a magnetic compound, such as $Fe_3O_4$, that is encapsulated by a plurality of amino organosilane groups. The organosilane groups can include 3-[2-(2-Aminoethylamino) ethylamino] propyl-trimethoxysilane (TAS). At least some of the organosilane groups can have amino and carboxylic acid substituents. The organic pollutants can include malachite green dye. The carboxylic functionalized magnetic nanocomposites can adsorb dye from solution, such as wastewater. The carboxylic functionalized magnetic nanocomposites can be separated from the solution using an external magnetic material.

13 Claims, 6 Drawing Sheets

(56) References Cited

U.S. PATENT DOCUMENTS

2009/0321363 A1    12/2009   Murai et al.
2013/0105397 A1    5/2013   Shukla et al.
2016/0243523 A1    8/2016   Saini et al.

OTHER PUBLICATIONS

McCarthy et al. "Preparation of multifunctional nanoparticles and their assemblies", Nature Protocols, 7, 1677-1693.*
De Palma, et al. "Silane Ligand Exchange to MAke Hydrophobic Superparamagnetic Nanoparticles Water-Dispersable", Chem Mater, 2007, 19, 1921-1831.*
Naghizadeh et al. (Iranica Journal of Energy & Environment, 2016, 7, 359-366).*
Esmaeilnejad-Ahranjani et al. (RSC Advances, 2015, 5, 33313-33327).*
Mishra, Rashmi Rani, Preethy Chandran, and S. Sudheer Khan. "Equilibrium and kinetic studies on adsorptive removal of malachite green by the citrate-stabilized magnetite nanoparticles." RSC Advances 4.93 (2014): 51787-51793.
Wang, Dongxue, et al. "Adsorption and removal of malachite green from aqueous solution using magnetic β-cyclodextrin-graphene oxide nanocomposites as adsorbents." Colloids and Surfaces A: Physicochemical and Engineering Aspects 466 (2015): 166-173.
Alqadami, Ayoub Abdullah, et al. "Efficient removal of toxic metal ions from wastewater using a recyclable nanocomposite: A study of adsorption parameters and interaction mechanism." Journal of Cleaner Production 156 (2017): 426-436.

* cited by examiner

CARBOXYLIC FUNCTIONALIZED MAGNETIC NANOCOMPOSITE

BACKGROUND

1. Field

The disclosure of the present patent application relates to a hybrid magnetic adsorbent for organic dye adsorption, and particularly, to a carboxylic functionalized magnetic nanocomposite for the removal of malachite green dye from a solution.

2. Description of the Related Art

Synthetic dyes are extensively used in various industries, including paint, printing, leather, rubber, plastic, textile, paper, pesticide, food, cosmetics, pigments, petroleum, solvent, wood preserving chemicals, and pharmaceutical industries. Over 10,000 different commercial dyes and pigments exist and more than $7 \times 10^5$ tonnes are produced annually worldwide. Dyes and dye by-products alter water chemistry. As such, industrial release of dyes or colored wastewater into natural bodies of water can bring about great harm to the environment, especially to aquatic animals, plants and humans.

Malachite green (MG) is a popular cationic dye, which is used for dyeing of paper, leather cotton, silk, and in manufacturing of paints and printing inks. MG is highly cytotoxic to mammalian cells and causes detrimental effects in kidney, intestine, gill, liver, gonads and pituitary gonadotropic cells. Although use of MG dye is banned in many countries and is not accepted by US FDA, it is still being used in many countries due to its low cost and easy availability. Therefore, treatment of effluent-containing malachite green dye pollutants before they are discharged to the environment is essential.

Various methods have been proposed for removal of dyes from wastewater, such as membrane separation, flocculation, electro-flotation, precipitation, coagulation and flocculation, ion exchange and adsorption. Among these methods, adsorption is regarded as an easy, economic and desirable process due to its high efficiency and ability to separate a wide range of pollutants from industrial effluents. Several adsorbents have already been used for the removal of malachite green dye from aqueous solutions, such as cyclodextrin-based adsorbent, degreased coffee bean, pine sawdust, sea shell powder, iron humate, prosopis cineraria, bagasse fly ash, oil palm trunk fiber, polyurethane foam, bentonite and carbon prepared from arundo donax root.

Thus, an adsorbent for organic pollutant removal solving the aforementioned problems is desired.

SUMMARY

Carboxylic functionalized magnetic nanocomposites can include a magnetic compound, such as $Fe_3O_4$, that is encapsulated by a plurality of amino organosilane groups. The amino organosilane groups can include 3-[2-(2-Aminoethylamino)ethylamino] propyl-trimethoxysilane (TAS). The organosilane groups can be substituted with amine and carboxylic acid functional groups. The organic pollutants can include malachite green dye. The carboxylic functionalized magnetic nanocomposites can adsorb dye from solution, such as wastewater. The carboxylic functionalized magnetic nanocomposites can be easily separated from the solution by application of an external magnetic field.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
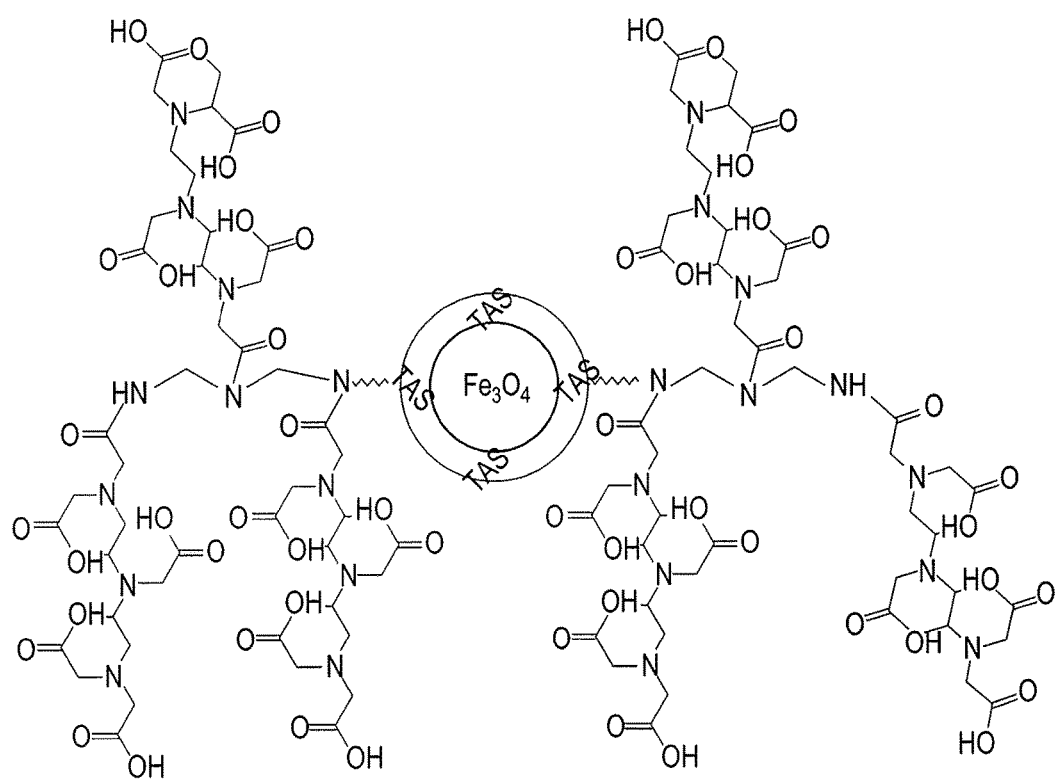
FIG. 1 shows the chemical structure of an exemplary carboxylic functionalized magnetic nanocomposite.

Carboxylic functionalized magnetic nanocomposites can include a magnetic compound, such as $Fe_3O_4$. The magnetic compound can be encapsulated by a plurality of amino organosilane groups. The organosilane groups can include 3-[2-(2-Aminoethylamino)ethylamino] propyl-trimethoxysilane (TAS). The organosilane groups can be substituted with amine and carboxylic acid functional groups. For example, diethylenetriaminepentaacetic dianhydride (DTPADA) can be attached to the magnetic support by first using silylating agents (TAS) and then reacting the surface bound amine groups with DTPA anhydride to induce amide bonds between amino groups of the organosilane and carboxyl group of DTPA. DTPADA is an octadentate ligand and includes amino carboxylic acids containing oxygen and nitrogen binding sites. The carboxylic functionalized magnetic nanocomposites or $Fe_3O_4$@TSPA nanocomposites, are shown in FIG. 1.

The carboxylic functionalized magnetic nanocomposites can have a high surface area. The surface area can be about 186 $m^2/g$. The carboxylic functionalized magnetic nanocomposites can be in powder form, e.g., a black, porous, solid powder. The carboxylic functionalized magnetic nanocomposites can be crystalline in nature.

Figure 2:
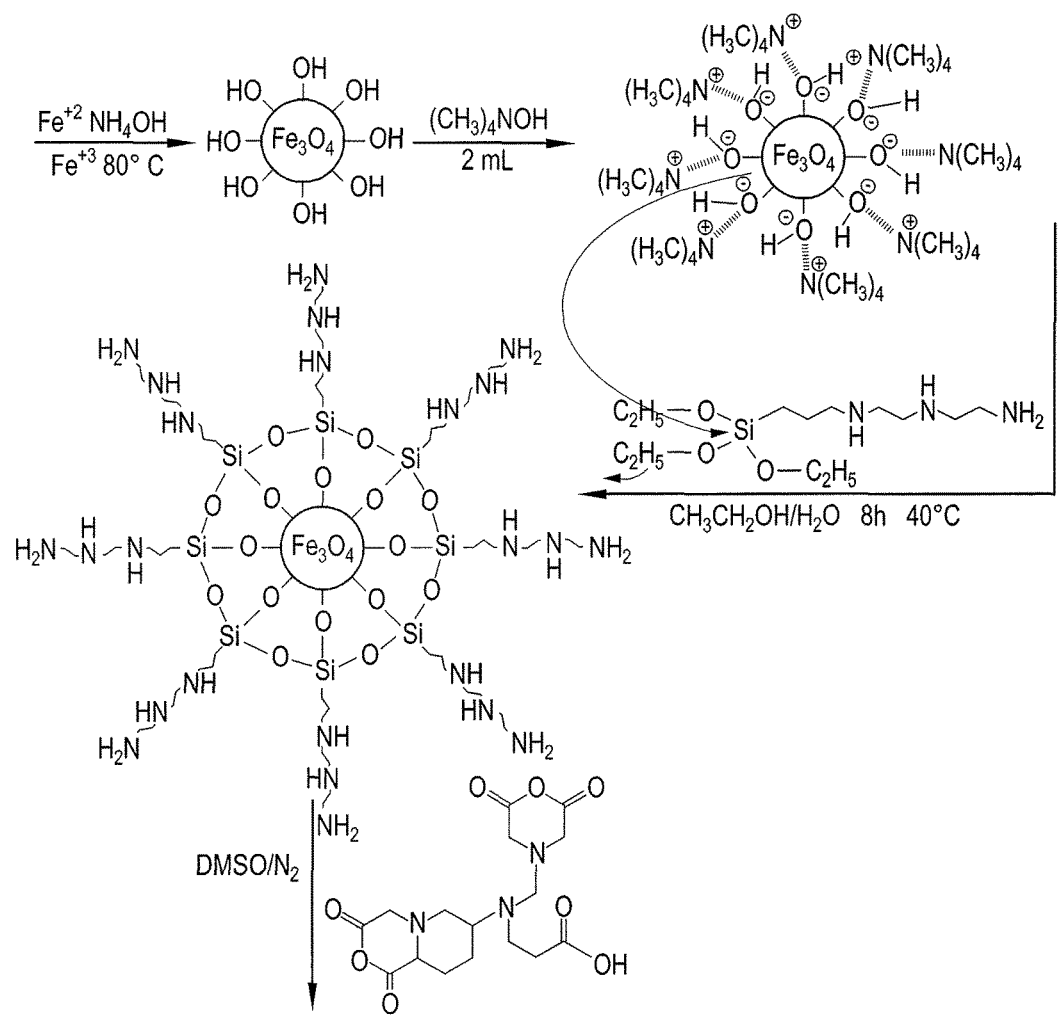
FIG. 2 shows an exemplary reaction scheme for synthesizing the carboxylic functionalized magnetic nanocomposite.

FIG. 2 depicts an exemplary reaction scheme for synthesizing the carboxylic functionalized magnetic nanocomposite. As shown in FIG. 2, iron (II) chloride and iron (III) chloride can be mixed, preferably in a 1:2 molar ratio, to provide a first mixture. The mixture can be heated at about 80° C. for about one hour. An aqueous basic solution, e.g., aqueous solution of $NH_4OH$, can be added to the heated mixture to form $Fe_3O_4$ nanoparticles. The $Fe_3O_4$ nanoparticles can be coated with a surfactant, such as tetramethylammonium hydroxide. The coated $Fe_3O_4$ nanoparticles can be dispersed in an aqueous alcohol solution, e.g., aqueous ethanol solution, to form a second mixture. An amino organosilane can be added to the second mixture to provide amine-grafted, coated $Fe_3O_4$ nanoparticles. The amino organosilane group can include 3-[2-(2-Aminoethylamino) ethylamino] propyl-trimethoxysilane (TAS). Diethylenetriaminepentaacetic (DTPA) anhydride can be dispersed in dimethyl sulfoxide (DMSO) to provide a clear solution. The amine-grafted, coated $Fe_3O_4$ nanoparticles can be added to the clear solution to provide the carboxylic functionalized magnetic nanocomposite.

The carboxylic functionalized magnetic nanocomposites can be used for pollutant removal from aqueous solution. The pollutants can include organic metal pollutants. The organic pollutants can include dyes, such as malachite green. The carboxylic functionalized magnetic nanocomposites can adsorb dye from solution, such as wastewater. The carboxylic functionalized magnetic nanocomposites can easily separate from the solution by application of an external magnetic field.

The nanocomposites can efficiently remove malachite green dye (>92.0%) from aqueous solution when contacted with the aqueous solution. Preferably, the nanocomposites are contacted with the aqueous solution for about 60 minutes. The treatment process of removing dyes from solution using the nanocomposites is clean and safe, as compared to existing methods. The adsorbed dye can be desorbed from the nanocomposites using a regenerating solution, comprising aqueous solution of 0.1 M HCl. Thus, the adsorbent nanocomposites can be efficiently used as an adsorbent for environmental pollution control.

The following examples are provided by way of illustration.

Example 1

Preparation of $Fe_3O_4$@ TMAOH Nanocomposite $Fe_3O_4$ nanoparticles were prepared in a three-necked, round bottom flask equipped with a mechanical stirrer, nitrogen gas inlet and dropping funnel by using a co-precipitation process. In the first step, iron(II) chloride and iron(III) chloride were mixed in 1:2 molar ratio. This ratio was achieved by dissolving 5.4 g $FeCl_3.6H_2O$ in 100 mL 0.1 M HCl and 1.99 g $FeCl_2.4H_2O$ in 100 mL 0.1 M HCl under $N_2$ gas for 30 min. The nitrogen gas was used to remove $O_2$ and to prevent the unwanted critical oxidation of Fe(II). Afterward, these two solutions were mixed with vigorous stirring and heated at 80° C. under $N_2$ for 1 h. An aqueous solution of $NH_4OH$ (28% 20 mL) was added drop-wise into the solution at the same temperature (80° C.) for 5 hrs. Black colored precipitates were obtained and isolated from the supernatant liquid by decantation. The precipitates were washed with demineralized water and separated using centrifugation at 5000 rpm for 10 min. To avoid particle agglomeration in ferrofluid, surfactant coating on the surface of the magnetic particles was used. The surfactant molecules create electrostatic force to repulse the particles from each other and prevent clumping. Tetramethylammonium hydroxide (($CH_3)_4NOH$), or TMAOH was used as surfactants for magnetite nanoparticles. The obtained $Fe_3O_4$ nanoparticles were suspended in TMAOH solution (4 mL 25%). The hydroxide anions were coated on $Fe_3O_4$ particles and the tetramethylammounium cations formed a shell for each particle, resulting in electrostatic repulsion among particles.

Example 2

Preparation of $Fe_3O_4$@TAS Nanocomposite

For preparation of $Fe_3O_4$@TAS nanocomposite, tri-amino-functionalized $Fe_3O_4$@TMAOH nanoparticles were synthesized by salinization reaction according to the procedure described earlier with some modification by using 3-[2-(2-Aminoethylamino)ethylamino] propyl-trimethoxysilane (TAS) as the silylation agent. In a typical experiment, 4 grams of $Fe_3O_4$@TMAOH nanoparticles were dispersed in ethanol (350 mL) and water (4 mL) by ultrasonication until it formed a clear dispersion for approximately 30 min. After that TAS (d=1.03 g/ml, 16 g, 12 ml) was added drop wise to the mixture for 24 hrs with a mechanical mixer with heating at 40° C. under a $N_2$ atmosphere to provide amine grafted $Fe_3O_4$@TMAOH particles. After completion of the reaction, the resultant amine grafted $Fe_3O_4$@TMAOH particles were washed several times with ethanol to remove the unreacted 3-[2-(2-aminoethylamino) ethylamino] propyltrimethoxysilane and dried at room temperature for 48 hrs. The materials obtained are referred to as $Fe_3O_4$@TAS nanocomposite.

Example 3

Figure 3:
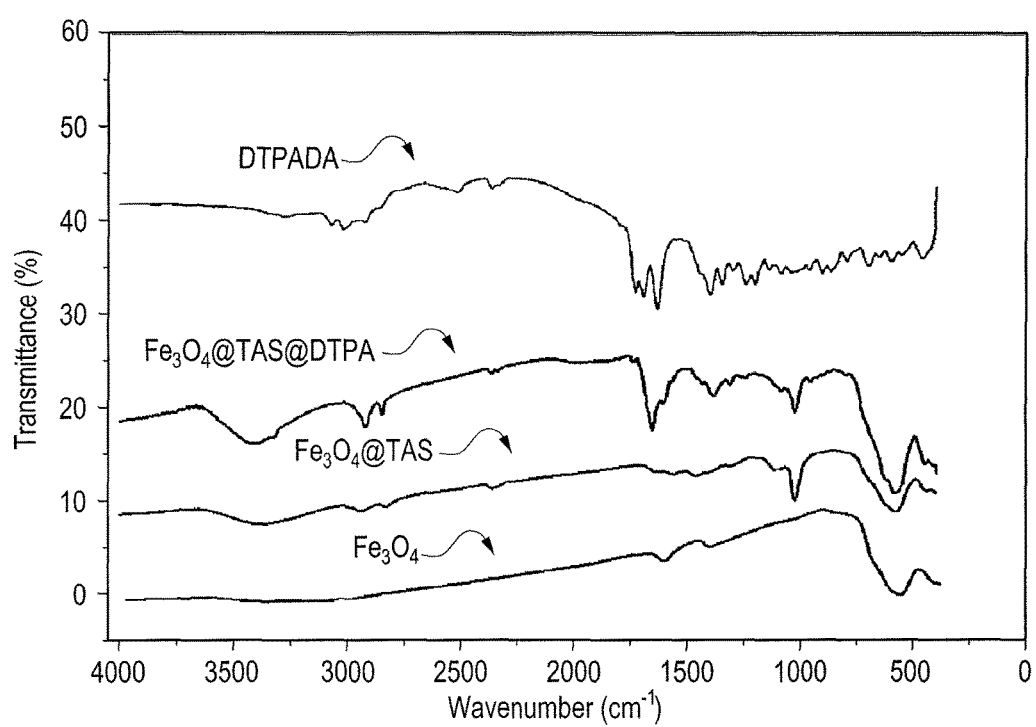
FIG. 3 is a graph showing the FTIR spectrum of the compounds shown in the reaction scheme of FIG. 2.
Figure 4:
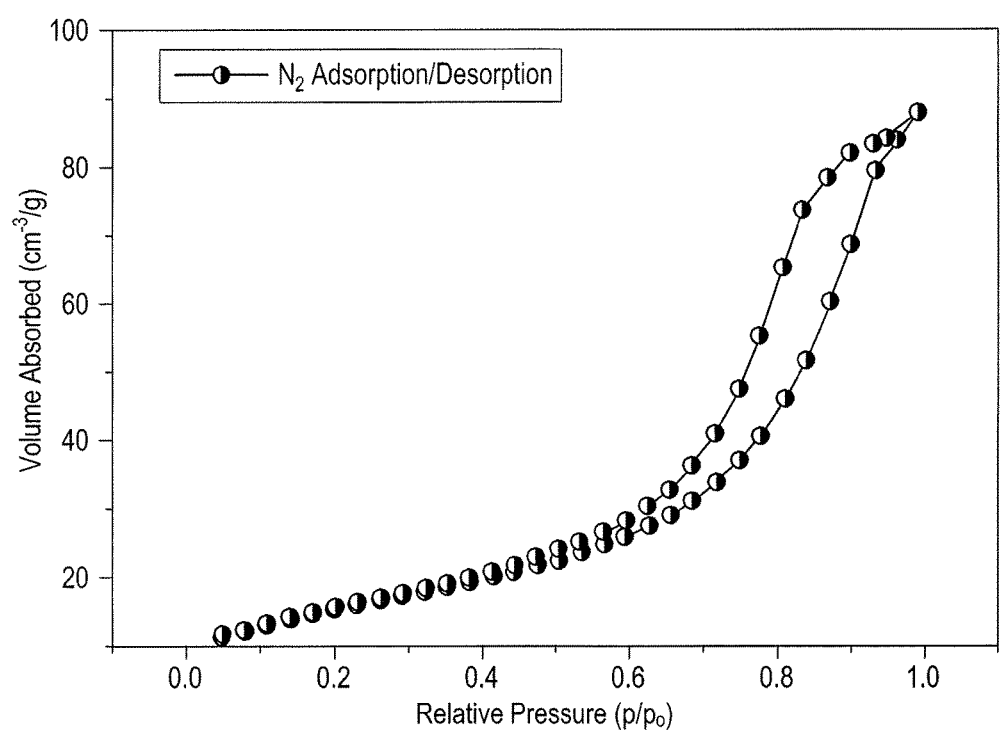
FIG. 4 is a graph showing the $N_2$ adsorption desorption isotherm of the carboxylic functionalized magnetic nanocomposite.
Figure 5:
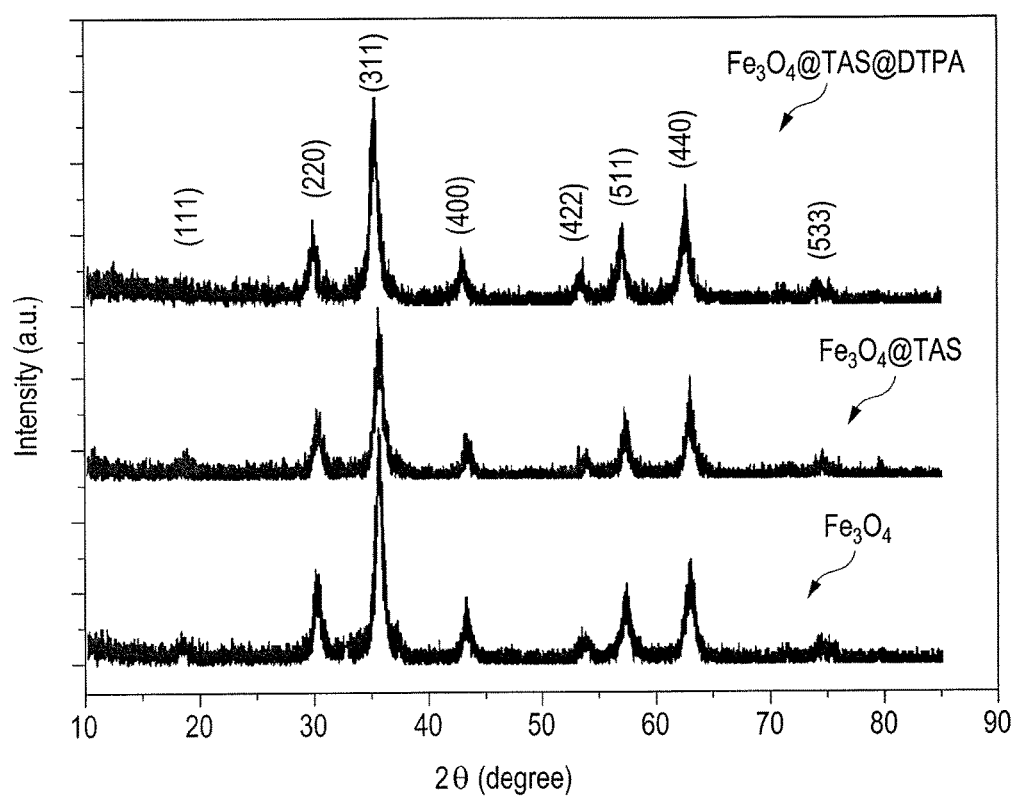
FIG. 5 shows the XRD spectrum of the compounds shown in the reaction scheme of FIG. 2.
Figure 6A:
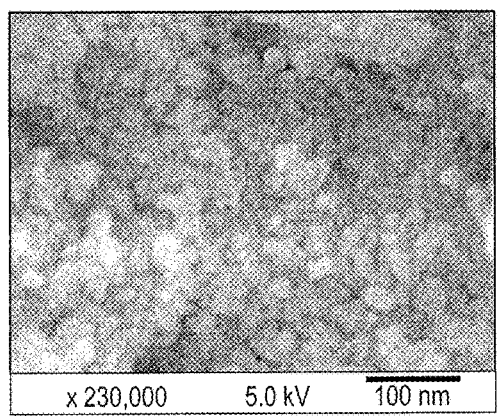
FIGS. 6A, 6B, and 6C show SEM images of the $Fe_3O_4$ nanoparticles, the $Fe_3O_4$@TAS nanocomposite, and the $Fe_3O_4$@TSPA nanocomposite, respectively.
Figure 6B:
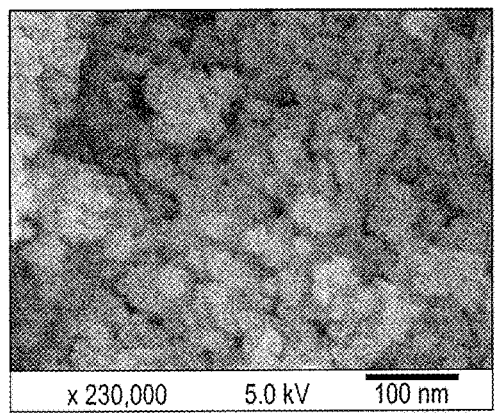
Figure 6C:
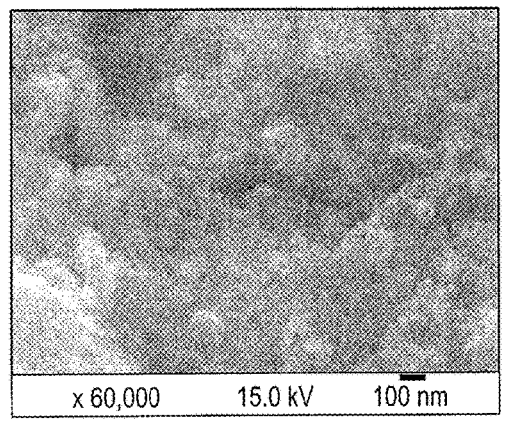

Synthesis of $Fe_3O_4$@TSPA Nanocomposite 3.21 g diethylenetriaminepentaacetic dianhydride (DTPADA) was dispersed in 80 mL DMSO under ultra-sonication for 40 min. to provide a clear solution. 1.45 g $Fe_3O_4$@TAS nanocomposite was added to solution under stirring and $N_2$ at room temperature overnight to form the $Fe_3O_4$@TSPA nanocomposite or carboxylic functionalized magnetic nanocomposite. Then, the nanocomposite particles were magnetically confined, washed with deionized water, and dried at room temperature. DTPA is able to form more stable chelates with metal ions of a coordination number of eight. The higher steric effect of DTPA was taken into consideration for some complex formations. The $Fe_3O_4$@TSPA nanocomposite was determined to be a black, porous, solid, crystalline structure. The FTIR spectrum and XRD spectrum of the $Fe_3O_4$ nanoparticle, the $Fe_3O_4$@TAS nanocomposite, and the $Fe_3O_4$@TSPA nanocomposite are provided in FIG. 3 and FIG. 5, respectively. The specific surface area of the $Fe_3O_4$@TSPA nanocomposite was 186 $m^2/g$. The $N_2$ adsorption desorption isotherm of the $Fe_3O_4$@TSPA nanocomposite is provided in FIG. 4. SEM images of the $Fe_3O_4$ nanoparticles, the $Fe_3O_4$@TAS nanocomposite, and the $Fe_3O_4$@TSPA nanocomposite, are provided in FIG. 6A, FIG. 6B, and FIG. 6C, respectively.

Example 4

Adsorption Procedure

The adsorption of malachite green dye onto carboxylic functionalized magnetic nanocomposite was carried out by a batch method. The adsorption experiments were performed in 100 mL glass conical flasks. Initially, about 25 mg adsorbent was added to 25 mL of malachite green dye solution of 100 ppm in a conical flask, which was placed in a thermostatic shaking assembly. The test flasks were sealed to prevent change in volume of the solution during the experiments. The solution was stirred continuously at a constant temperature for a certain time to achieve equilibration. After equilibration, the magnetic nanocomposite was separated using an extremal magnetic field. The concentrations of malachite green dye in the solution phase before and after adsorption were determined using a double beam UV-Vis spectrophotometer at 620 nm. A number of parameters (such as contact time, pH, initial malachite green concentration and temperature) were changed in order to optimize the adsorption process. The process was carried out at room temperature. The pH was adjusted between pH 2 and pH 11, with maximum adsorption being at pH 7. The adsorption rate increased with increased contact time. The equilibrium time was 60 minutes. The adsorption capacity was calculated to be 145 mg g$^{-1}$ at 60 minutes. The adsorption capacity was decreased with increasing the concentration of the malachite green dye in aqueous solution. The optimum dose of the adsorbent was 50 mg/25 mL.

The amount of adsorbed malachite green dyes at equilibrium, qe(mg/g), and the percent adsorption (%) of malachite green dyes were computed as follows:

$$qe=V(C_0-C_e)W\times 1000,$$

where, V is the volume of malachite green dye solution in liters, $C_0$ and $C_e$ are the initial and final concentrations (mg L$^{-1}$) of malachite green dye in solution, and W is the weight of adsorbent in grams.

The exhausted adsorbent can be separated from solution using an external magnetic field. The adsorbed dye can desorbed from the adsorbent using a regenerating solution including 0.1 M HCl.

It is to be understood that the carboxylic functionalized magnetic nanocomposite for the removal of organic pollutant removal is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A carboxylic functionalized magnetic nanocomposite, comprising:
    a magnetite (Fe$_3$O$_4$) nanoparticle core;
    an organosilane group encapsulating the magnetite (Fe$_3$O$_4$) nanoparticle core, wherein the organosilane group comprises 3-[2-(2-aminoethylamino)ethylamino] propyl-trimethoxysilane (TAS); and
    a plurality of amino carboxylic acid functional groups attached to the organosilane group.

2. The carboxylic functionalized magnetic nanocomposite according to claim 1, wherein the carboxylic functionalized magnetic nanocomposite has a surface area of about 186 m$^2$/g.

3. The carboxylic functionalized magnetic nanocomposite according to claim 1, wherein the carboxylic functionalized magnetic nanocomposite is in powder form.

4. A method of synthesizing a carboxylic functionalized magnetic nanocomposite, comprising:
    mixing iron (II) chloride and iron (III) chloride in a 1:2 molar ratio to provide a first mixture;
    heating the first mixture at about 80° C. for about one hour to form a heated mixture;
    adding NH$_4$OH to the heated mixture to form Fe$_3$O$_4$ nanoparticles;
    coating the Fe$_3$O$_4$ nanoparticles with a surfactant;
    dispersing the coated Fe$_3$O$_4$ nanoparticles in an aqueous alcohol solution to form a second mixture;
    adding 3-[2-(2-aminoethylamino)ethylamino] propyl-trimethoxysilane (TAS) to the second mixture to provide amine-grafted, coated Fe$_3$O$_4$ nanoparticles;
    dispersing diethylenetriaminepentaacetic (DTPA) dianhydride in dimethyl sulfoxide (DMSO) to provide a clear solution; and
    adding the amine-grafted, coated Fe$_3$O$_4$ nanoparticles to the clear solution to provide the carboxylic functionalized magnetic nanocomposite.

5. The method of synthesizing a carboxylic functionalized magnetic nanocomposite according to claim 4, wherein the surfactant comprises tetramethylammonium hydroxide.

6. A method of removing an organic pollutant from a liquid medium, comprising:
    contacting the liquid medium with the carboxylic functionalized nanocomposite of claim 1.

7. The method according to claim 6, wherein the liquid medium comprises water.

8. The method according to claim 6, wherein the organic pollutant comprises malachite green dye.

9. The method according to claim 6, wherein the contacting is at room temperature.

10. The method according to claim 6, further comprising the step of adjusting the pH of the liquid medium to pH 7.

11. The method according to claim 6, wherein an optimum dose of the carboxylic functionalized magnetic nanocomposite is about 50 mg/mL.

12. The method according to claim 6, further comprising separating the carboxylic functionalized magnetic nanocomposite from the liquid medium by applying an external magnetic field.

13. The method according to claim 6, further comprising regenerating the carboxylic functionalized magnetic nanocomposite using 0.1 M HCl solution.

* * * * *